Figure 1:
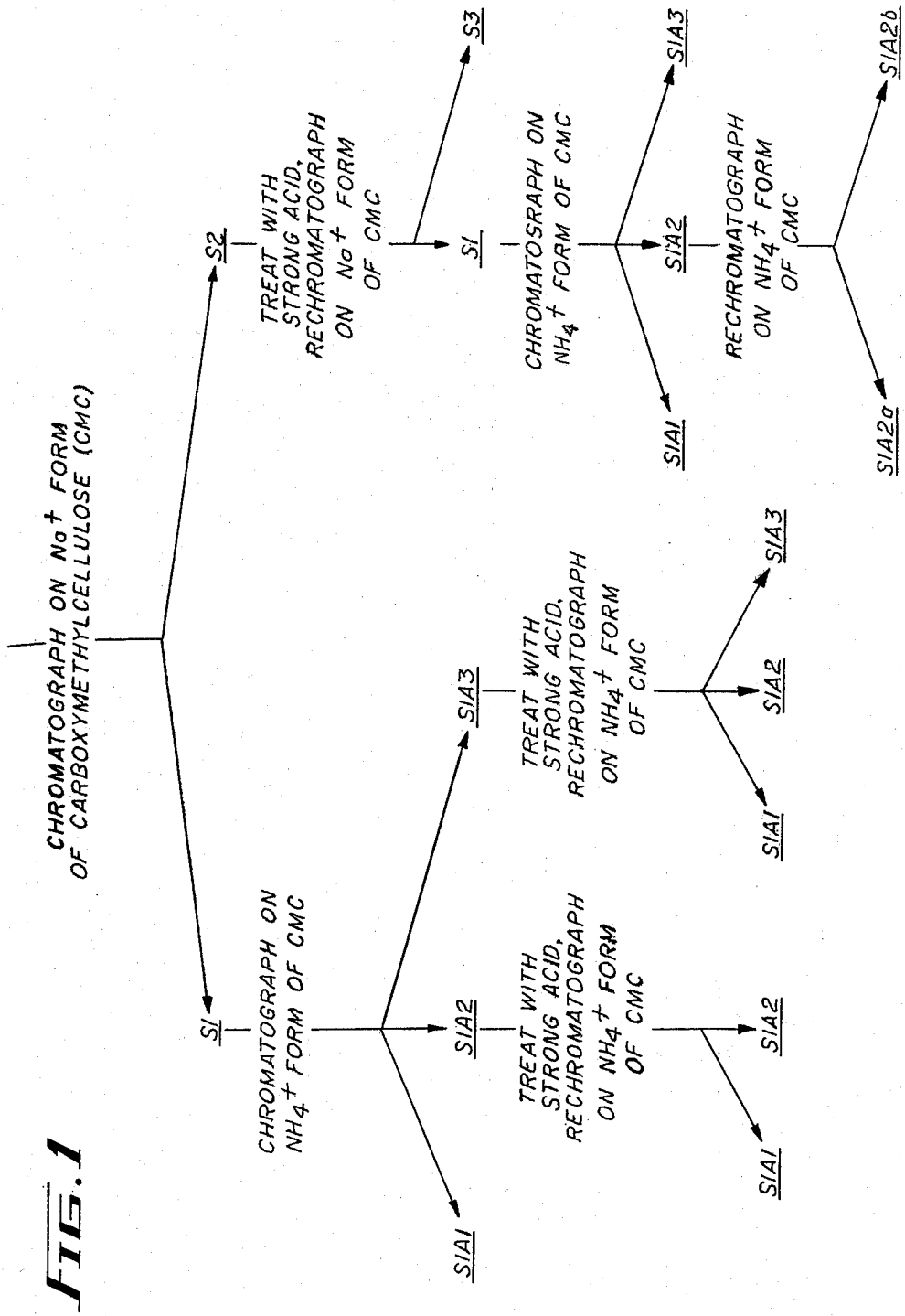

United States Patent [19]

Brockman

[11] 3,989,819

[45] Nov. 2, 1976

[54] PROCESS FOR SEPARATING PROTEINS FROM CENTRAL NERVOUS SYSTEM TISSUE AND TREATING EXPERIMENTALLY INDUCED DEMYELINATING DISEASES

[75] Inventor: John A. Brockman, Woodcliff Lake, N.J.

[73] Assignee: American Cyanamid Company, Stamford, Conn.

[22] Filed: Oct. 26, 1971

[21] Appl. No.: 191,982

Related U.S. Application Data

[63] Continuation-in-part of Ser. No. 804,494, March 5, 1969, abandoned.

[52] U.S. Cl. ................................................ 424/95
[51] Int. Cl.² ................. A61K 35/12; A61K 35/56
[58] Field of Search ....................................... 424/95

[56] References Cited
OTHER PUBLICATIONS

Merck Manual, 12th Edition, 1972, pp. 1339–1342.
Chemical Abstracts, vol. 53, 16348a (1959).

*Primary Examiner*—Norman A. Drezin
*Attorney, Agent, or Firm*—Jack W. Richards

[57] ABSTRACT

There is described a process for the preparation and separation of components from central nervous system tissue by sequential chromatography; wherein certain components contain proteins of a weight average molecular weight of 8,000 to 10,000 and are highly encephalitogenic while others have weight average molecular weights in the range of 2,000 to 4,000 and exhibit weaker encephalitogenic activity, and in addition, a method of treating experimentally induced diseases by administering said low molecular weight components is described.

11 Claims, 5 Drawing Figures

PROCESS FOR SEPARATING PROTEINS FROM CENTRAL NERVOUS SYSTEM TISSUE AND TREATING EXPERIMENTALLY INDUCED DEMYELINATING DISEASES

CROSS REFERENCE TO RELATED APPLICATION

This application is a continuation-in-part of my application Ser. No. 804,494, now abandoned filed Mar. 5, 1969.

BRIEF SUMMARY OF THE INVENTION

This invention relates to methods of preparation and isolation of materials from mammalian central nervous system tissue which are of high encephalitogenic activity or of low encephalitogenic activity possessing high protective activity against experimentally induced demyelinating diseases.

BACKGROUND OF THE INVENTION

Various diseases of the nervous system involving myelin damage are known. Some, such as, for example, encephalomyelitis, can be produced in typical laboratory test mammals by sensitizing with certain fractions of material from mammalian central nervous tissue, such as bovine spinal cord. Such a disease is experimental allergic encephalomyelitis. An example of an encephalitogen is the large protein, about 142 amino acids, which is described in an article by Eylar and Hashim, in Vol. 61, *Proceedings* of the National Academy of Science, August 1968, pgs. 644–650. This protein was referred to by the author as the "A1" protein. In the article there is described enzymatic digestion of the A1 protein to produce shorter chain fragments, and the authors found that two such fragments, which they labelled "E" and "E1", of 16 and 26 amino acids respectively contained all of the encephalitogenic activity of the whole A1 protein.

Protection against diseases often involves introducing the protective agents into the animal before challenge, and generally this results in the formation of antibodies which then prevent the disease or ameliorate symptoms. In autoimmune demyelinating diseases, the role played by antibodies has not been conclusively determined. It appears that a number of other factors, not well known, are probably involved.

The present invention involves a process for separating the crude basic protein obtained from mammalian central nervous system tissue, such as bovine spinal cord tissue, into fractions of different encephalitogenic properties by chromatography.

The crude basic protein utilized in this invention is isolated from mammalian central nervous system tissue after the tissue is defatted by extraction with an organic solvent or solvent mixture capable of dissolving lipids in the presence of water, examples are ketonic solvents, chloroform-methanol, fluorocarbon-ethanol, etc. It should be noted that dehydration usually accompanies the defatting process; however, this is not an essential step. The actual isolation of the crude basic protein involves a simple acid extraction of the defatted mammalian central nervous system tissue. Generally, the tissue is successively extracted with water, aqueous NaCl and water at low pH's. Dilute acid of a pH between 1.5–2.5 extracts the crude basic protein which is then salted out, dissolved in water, dialyzed and freeze-dried. Other standard acid extraction methods may be employed with the provision that the conditions not be such as to cause any significant degree of degradation of the tissue. It should be further noted that the central nervous system tissue for these extractions can be spinal cord tissue or brain tissue and can be obtained from any number of different mammalian species including but not limited to horse, mouse, guinea pig, rabbit, monkey and man. Aside from the practical limitation of availability the only requirement is that the donor animal must be of sufficient age so that development in the central nervous system has progressed to the stage of myelination, since the crude basic proteins are subfractions of myelin.

The invention more specifically relates to the separation of fractions by chromatographing the crude basic protein and the rechromatographing of sub-fractions or reaction products of sub-fractions obtained from central nervous system tissue. The terms used to designate the various fractions isolated are meant only to show the relation of the components to each other.

The crude basic protein is dissolved in about 0.005M to about 0.015M sodium carbonate in about 0.01M to about 0.09M ammonium hydroxide solution and carefully placed on the column containing the sodium form of carboxymethylcellulose. The column is next eluted with about 0.01M to about 0.03M sodium chloride in about 0.01M to about 0.09M ammonium hydroxide followed by a developing solution in which the concentration of the sodium chloride is increased to about 0.1M to about 0.5M. Two fractions are isolated after desalting and freeze drying, S1, a material having a weight average molecular weight of 2,000 to 4,000 and low encephalitogenic activity, and S2 a material having a weight average molecular weight of 8,000 to 10,000 and a high degree of encephalitogenic activity. It has also been found that treatment of the S2 fraction with about 5N to 7N strong acid, preferably hydrochloric acid also gives rise to S1 material. The acid concentration is not critical since a lowering of concentration of the acid may be compensated for by increasing the time of treatment. The S2 fraction, after acid treatment followed by removal of the acid, usually by use of gel filtration of an ion exchange resin, and drying, preferably freeze-drying, was chromatographed in the same manner as the crude basic protein. In fact, crude basic protein itself can be treated directly with strong acid to form increased amounts of S1 material which can be isolated as described. The S1 material isolated from the material treated with acid has a weight average molecular weight of 2,000 to 4,000 and is of low encephalitogenic activity. While it very closely resembles the S1 material obtained directly from the crude basic protein, the two materials probably are not identical although very closely related. A second fraction S3, also obtained from the acid treatment of S2 is of about the same weight average molecular weight as S2, that is 8,000 to 10,000, but of a slightly lesser encephalitogenic activity. This S3 material can be treated again with strong acid and processed as described to yield additional S1 material.

It has also been found that the S1 fractions can be rechromatographed on the ammonium form of carboxymethylcellulose. The S1 fraction, dissolved in about 0.005M to about 0.02M ammonium chloride in about 0.005M to about 0.02M ammonium hydroxide, is applied to the column which is then eluted with the same ammonium chloride-ammonium hydroxide solution. After a period of time the concentration of the eluent is increased to about 0.1M to about 0.5M ammonium chloride-ammonium hydroxide solution. The fractions are desalted and freeze dried.

The S1 fraction obtained directly from the crude basic protein of central nervous system tissue gives three sub-fractions S1A1 the first to be eluted from the column, S1A2, the second, and S1A3, the third. These fractions have weight average molecular weights of 2,000 to 4,000 and are of low encephalitogenic activity.

The S1 fraction obtained from a fractionation of the acid treated S2 fraction gives four fractions (see FIG. 1). These components are eluted in the following order, S1A1, S1A2 (which appears to be a mixture of S1A2$a$, S1A2$b$) and S1A3. The weight average molecular weight of these components is 2,000 to 4,000 and these materials possess weak encephalitogenic activity. The components obtained from the rechromatographing of the S1 obtained from the acid treated S2 material and the S1 obtained directly from the crude basic protein of central nervous system tissue are very similar in all their characteristics; however, some minor structural differences probably are present.

Another aspect of the invention is a rather remarkable protection which results when large doses of the low molecular weight materials are given to animals, such as guinea pigs, sensitized with an encephalitogen, for example 15 $\mu$g of S2 material. Untreated guinea pigs sensitized in this way typically develop encephalomyelitic symptoms over a period of two to four weeks, whereas animals treated with massive doses, 1-mg. doses repeated ten times from the 7th to the 18th day for a total of 10 mg., are protected, in some cases completely and in other cases to a marked extent. The mechanism whereby the treatment with low encephalitogenic material in massive doses after challenge with sufficient material to cause serious disease and/or death is not known. It is, therefore, not intended to limit this aspect of the present invention to any theory of why such great protection results from treatment with weakly encephalitogenic material after sufficient sensitization to normally result in a serious disease onset. The results, however, are quite dramatic, and of course very useful, because this permits effective treatment of useful mammals after sensitization which would otherwise cause serious disease or death. When it is attempted to treat with smaller doses before challenge there is also sometimes some amelioration but not the dramatic protection obtainable with the doses after challenge.

Others have observed and reported before such protection using highly encephalitogenic proteins, but achieving such protection with weakly encephalitogenic materials is a novel and important part of the present invention.

Because of the convenience and cheapness of using guinea pigs and their high sensitivity they are very useful as laboratory test animals. Thus specific data in the experiments is shown with this animal instead of with some of the larger, more useful mammals, such as horses, dogs and the like.

Because of the ease of producing experimental encephalomyelitis in quinea pigs, this is the form of demyelinating disease which is specifically and quantitatively described. It should be understood, however, that the invention is not limited thereto and is applicable also to the whole spectrum of diseases which result in degradation or inflamation of the myelin sheaths of nerves.

BRIEF DESCRIPTION OF THE DRAWINGS

FIG. 1 is a flow sheet showing how chromatography on the sodium form of carboxymethylcellulose and on the ammonium form can be used to separate from crude basic protein the desired fractions, S1 and its sub-fractions, and how ultimate use of chromatography and treatment with strong acid can be used to prepare additional amounts of these fractions from S2. It also shows the sequential conversion of S1A3 to S1A2 to S1A1 by strong acid.

FIG. 2 is a chart showing some typical yields obtained when some of the procedures diagrammed in FIG. 1 are carried out.

FIG. 3 is a chromatogram showing the separation of S1 and S2 according to the flow sheet of FIG. 1.

FIG. 4 is a chromatogram showing the separation of S1 into its component, S1A1, S1A2, and S1A3, according to the flow sheet of FIG. 1.

FIG. 5 is a series of chromatograms according to the flow sheet of FIG. 1 showing (a) the separation of S1 material obtained from acid treated S2 material into S1A1, S1A2 and S1A3, (b) the rechromatography of S1A2 to separate **S1A2*a* and S1A2*b*, (c) the rechromatography of S1A2*a* to give a purer S1A2*a*, and (d) the rechromatography of S1A2*b* to give a purer S1A2*b*.**

EXAMPLE 1

Twenty-one grams of fresh guinea pig brains were chopped with 130 ml. absolute ethanol and 42 ml. of FREON 113* (unsymmetrical trifluorotrichloroethane) and filtered. The filter cake was washed successively with 100 ml. of 1:1 ethanol-FREON and 50 ml. of FREON and then dried under vacuum. The yield of defatted dehydrated tissue was 2.5 g.

This was extracted at 4° C. first with 75 ml. water, then successively with 25 ml. portions of 10% sodium chloride, water, and several times with 0.01N hydrochloric acid. The acid extracts with pH between 3.7 and 1.8 were combined and treated with an equal volume of saturated ammonium sulfate. The resulting precipitate was collected by centrifugation, taken up in 100 ml. of water, dialyzed, and freeze-dried to yield 50 mg. of crude basic protein.

EXAMPLE 2

Spinal cords were purchased from a slaughter house and were delivered packed in ice. The meninges were carefully removed from each cord, and if necessary the cleaned tissue was stored overnight in the cold (4° C.). Defatting and dehydration were carried out at room temperature on convenient size batches (usually 3 to 5 kg. wet weight) as follows. The tissue was chopped in a Waring Blender with FREON 113* and ethanol in the proportions of 1.0 kg. of cord tissue to 6.2 l. of alcohol to 2.0 l. of FREON. The mixture was then allowed to stand for at least one hour, and when necessary for convenient scheduling, overnight. It was then filtered, and the solids were blended again this time with 4.0 l. of 1:1 FREON-ethanol. After standing about one hour, or some convenient longer time, the mixture was again filtered, and the solids were washed with FREON and dried in vacuo or overnight in air to give defatted dehydrated spinal cord. This product still contained a small amount of fatty material, and a somewhat better product could be obtained with very little loss by one additional blending and extraction with 1:1 FREON-ethanol using ca. 8 to 10 l. of solvent per kg. of dry solids, followed by filtration, a FREON wash, and air drying. It is convenient to carry out this final extraction after accumulating and pooling several smaller batches.

In three different runs, yields were respectively: 1.90 kg. from 19.2 kg., 3.61 kg. from 37.5 kg., and 2.45 kg. from 24.6 kg. Thus the defatted dehydrated cord averaged ca. 9.8% of the wet weight of the cords after removal of the meninges.

The defatted dehydrated spinal cord was extracted in the cold 4° C. by dispersing in the desired solution in a Waring Blender (batchwise) for a few minutes, stirring gently for ca. two hours, allowing the mixture to stand overnight, and centrifuging in a refrigerated Sharples centrifuge. Successive extractions of 1.9 kg. of defatted dehydrated spinal cord were made as follows: 20 l. of water, 20 l. of 10% sodium chloride, 20 l. of water, 30 l. of water adjusted to pH 3.7 with hydrochloric acid, and finally 40 l. of water adjusted to pH 2.0 with hydrochloric acid. Only the last (pH 2.0) extract was saved. To it was added an equal volume (40 l.) of saturated ammonium sulfate (4° C.). The resulting precipitate was collected by centrifugation in a continuous Servall centrifuge, taken up in 10 l. of water, dialyzed against 100 l. of water, and freeze-dried to give 21.7 g. of crude basic protein.

In a second run the blending was done in an Eppenbach Blender, and the procedure was simplified so that 3.6 kg. of defatted dehydrated spinal cord was extracted successively with 40 l. of water, 40 l. of 10% sodium chloride, 40 l. of water adjusted to pH 3.8 and finally with 80 l. of water adjusted to pH 1.8–1.9 with 6 N hydrochloric acid. The precipitate from ammonium sulfate addition was collected by centrifugation, taken up in 20 l. of water, dialyzed against 100 l. of water (seven changes). After clarification by centrifugation the retentate was freeze-dried to yield 40 g. of crude basic protein.

In a third run 2.85 kg. of defatted dehydrated spinal cord was extracted essentially as described for the second run above, but dialysis was not carried out so thoroughly since in the meantime we had learned that the active basic protein itself might be somewhat dialyzable. The resulting 52.5 g. of crude material which contained considerable ammonium sulfate was desalted in 5-g. batches by gel filtration to give pooled yield after freeze-drying of 21.5 g. of crude basic protein.

Crude basic protein prepared in this manner was used as starting material in all the following examples.

EXAMPLE 3

Figure 2:
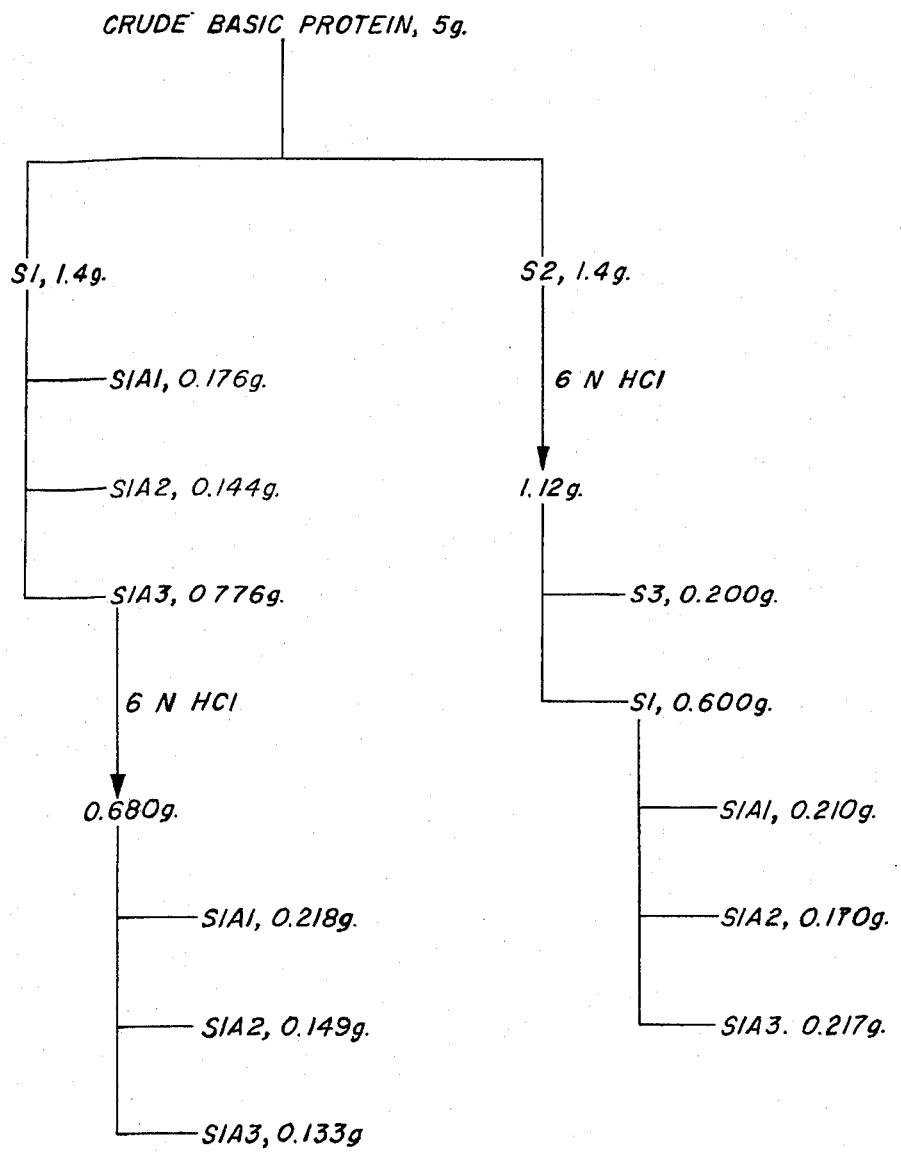

This example should be read in conjunction with FIGS. 1 and 2. Carboxylmethylcellulose was soaked in water for several hours, washed free of cations with 0.1N hydrochloric acid and then washed free of acid with distilled water. A slurry in water was adjusted to pH 8 to 9 with sodium hydroxide, thus producing the carboxymethylcellulose in the sodium form. A 100 ml. column, (2.8 cm diameter × 16 cm length), was packed with the slurry and the packed bed washed with several volumes of 0.02M sodium chloride in 0.05M ammonium hydroxide. This constituted the chromatographic column.

A 1-gram sample of crude basic protein was dissolved in 60 ml. of 0.01M sodium carbonate in 0.05M ammonium hydroxide. The solution was clarified to remove insoluble material and then was allowed to percolate into the chromatographic column. The column was then developed with the sodium chloride-ammonium hydroxide solution described above until about 200 ml. of the effluent had been collected. The developing solution was then changed by increasing the sodium chloride content to 0.3M, and development contained until an additional 200 ml. of effluent had been collected. The flow rate was approximately 195 ml./hr., and the effluent was monitored for optical density at 254 mu.

Figure 3:
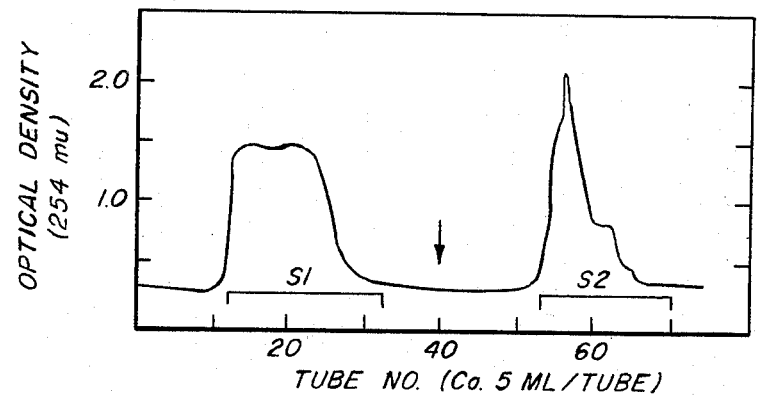

Development with the first sodium chloride-ammonium hydroxide solution produced a broad band of optical density appearing in the effluent between about 60 and 150 ml., and the development with the stronger sodium chloride solution produced several overlapping bands between about 270 and 350 ml., constituting a second cut. FIG. 3 shows the chromatogram of the procedure just described, the arrow indicating the point at which the developing solution was changed from 0.02M sodium chloride to 0.3M sodium chloride. The designation of the products, S1 and S2, is in accordance with FIG. 1. The above described procedure was repeated for five runs to obtain larger quantities of the two products which were desalted and freeze-dried.

The S1 material was then chromatographed in accordance with FIG. 1 using carboxymethylcellulose washed free of cations as described and slurried at a pH of about 9 with ammonium hydroxide to make the ammonium form. A 250 ml. column, (4.4 cm diameter × 16.5 cm length), was then packed with this slurry and the packed bed washed with several volumes of 0.3M ammonium chloride in 0.3M ammonium hydroxide, followed by a few volumes of 0.01M ammonium chloride in 0.01M ammonium hydroxide. A 700-mg. sample of S1 material produced as described above was then dissolved in the 0.01M ammonium chloride-ammonium hydroxide solution, the pH dropped to about 7. The solution was percolated through the column, and development was continued with the 0.01M ammonium chloride-ammonium hydroxide solution until about 525 ml. of effluent had been collected. The developer was then changed to the 0.3M ammonium chloride-ammonium hydroxide solution, and an additional 400 ml. of effluent was collected. The flow rate in this column was about 210 ml/hr, and the effluent was monitored for optical density as has been described. Two fairly well separated bands emerge between 180 and 350 ml. of effluent for the first cut and between about 375 and 475 ml. for the second cut. Development with the 0.3M ammonium chloride-ammonium hydroxide solution caused a band to appear between about 720 and 855 ml, constituting a third cut. Each cut was then acidified to pH 2 to 3 and retained.

Figure 4:
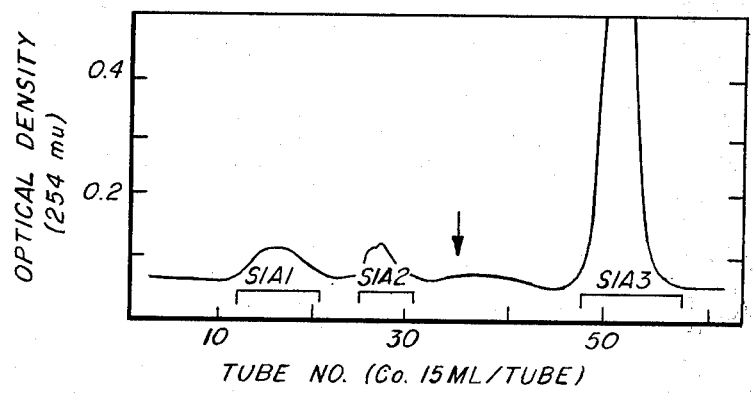
Figure 5:
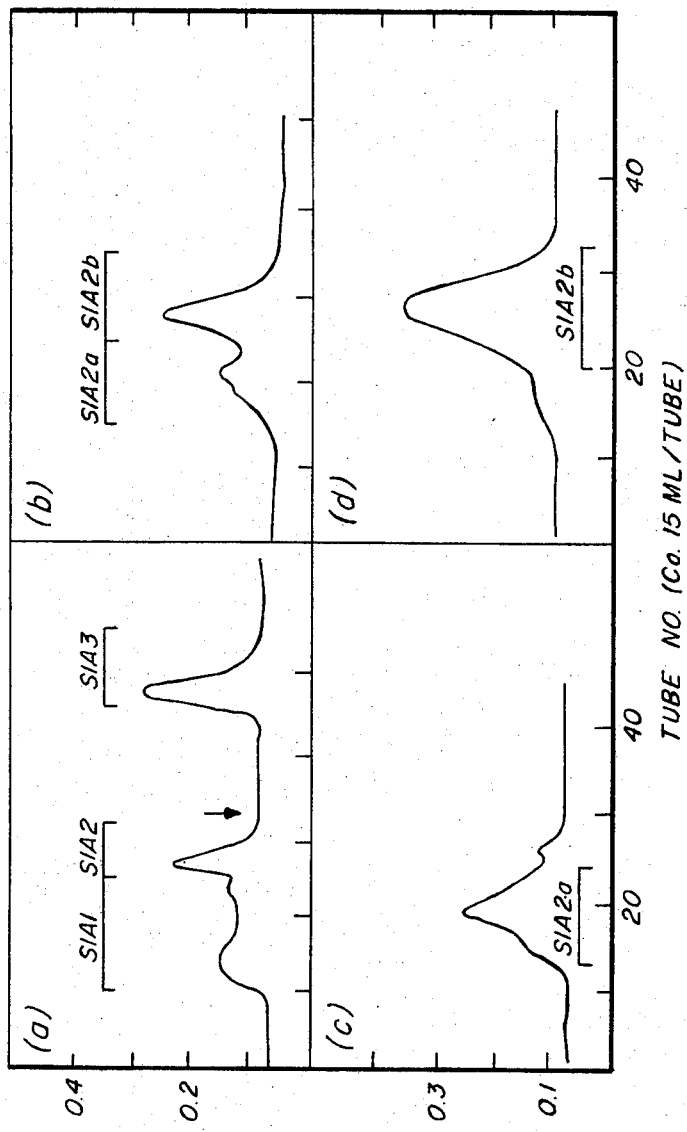

The column was washed with a few volumes of the 0.01M ammonium chloride-ammonium hydroxide solution and a second 700-mg. sample of the S1 material run through as described above. The cuts were pooled, desalted and freeze-dried, the first cut being referred to as S1A1, the second cut S1A2, and the third cut S1A3. FIG. 4 shows the chromatogram of the procedure just described, the arrow again indicating the change from the weaker to the stronger ammonium chloride-ammonium hydroxide solution.

FIGS. 1 and 2 show an acid treatment of the S2 material and also an acid treated S1A3 material and an acid treated S1A2 material from the chromatography of the S1 material described above. The S1A1, S1A2 and S1A3 had similar properties regardless of whether they were obtained by chromatography S1 or chromatography acid treated S1A3 or S1A2 or acid treated S2. In the last case, however, an attempt was made to separate S1A2, which is shown in the chromatograms of FIG. 5. There were two products, S1A2*a* and S1A2*b*.

EXAMPLE 4

In Example 1 and in FIGS. 1 and 2 reference is made to acid treatment of various fractions. All such treatments were carried out in a similar way although times and acid concentrations can be varied. A typical example, in which crude basic protein itself was treated, follows.

Four grams of crude basic protein were dissolved in 20 ml. of 6 N hydrochloric acid and allowed to stand at room temperature (ca. 22° C.) for 15 hours. The solution darkened on standing. The solution was diluted by adding 100 ml. of distilled water, and excess acid was removed by passing this solution through a one liter gel filtration column equilibrated with 0.001M hydrochloric acid. The effluent containing the protein (as determined by optical density) was freeze-dried to yield 3.4 g. (83%) of fluffy white product.

EXAMPLE 5

In vivo activity of the materials was determined by injecting the material intradermally in Freund's adjuvant. To evaluate disease response animals were graded on a scale from 0 for symptom free to 4 for dead. When a group of animals is considered the significant figure is the average worst symptom, i.e., the numerals for worst symptom for each animal were averaged. In five experiments averages ran as follows:

| | | Sensitizing Dose (μg) | Av. Worst Symptom |
|---|---|---|---|
| 5 Values | S2 | 15 | 2.30 |
| 2 Values | S1A1 | 150 | 0.32 |
| 3 Values | S1A2 | 150 | 0.05 |
| 6 Values | S1A3 | 150 | 0.52 |

The protective activity of S1A1, S1A2*a*, S1A2*b*, and S1A3 was demonstrated in the following experiment. Groups of 10 animals were sensitized with 15 μg. of S2. One group, the control, received no treatment doses. The others were treated by intraperitoneal injection of the treatment doses. The results are shown in the following table:

| | | Clinical Signs | | |
|---|---|---|---|---|
| | Treatment Dose (mg) | None | Dead | Av. Worst Symptom |
| S2 | none | 3 | 4 | 2.25 |
| S1A2a | 2 | 6 | 0 | 0.43 |
| | 10 | 10 | 0 | 0.00 |
| S1A2b | 2 | 6 | 1 | 0.68 |
| | 10 | 9 | 0 | 0.15 |
| S1A3 | 2 | 8 | 2 | 0.80 |
| | 10 | 10 | 0 | 0.00 |
| S1A1 | 2 | 6 | 2 | 1.10 |
| | 10 | 8 | 0 | 0.35 |

Where the dose was 2 mg, this was a preliminary intraperitoneal injection two days before sensitization. In the lines where the dose was 10 mg. there were ten 1 mg. doses, also by intraperitoneal injection in a saline solution, on days 7, 8, 9, 10, 11, 14, 15, 16, 17, and 18 following the sensitization with S2. It will be seen that with the 10 mg. treatment there was complete protection with S1A3 and S1A2*a*, and a high protection with S1A2*b* and S1A1. When the treatments, (2 mg), were prior to sensitization the protection was less than for the successive 1 mg. doses after sensitization.

I claim:

1. A process for separating components with weight average molecular weights of approximately 2,000 to 4,000 having weak encephalitogenic activity and high protective activity from the crude basic protein derived from defatted myelinated mammalian central nervous system material, which comprises dissolving said mammalian central nervous system material in a solution of about 0.005M to about 0.015M sodium carbonate in about 0.01M to about 0.09M ammonium hydroxide, chromatographing said solution containing mammalian central nervous system material on carboxymethylcellulose having sodium cations, eluting said chromatographed solution with approximately 0.01M to 0.03M of sodium chloride in approximately 0.01M to 0.09M ammonium hydroxide solution, collecting said eluate and recovering said components from said eluate.

2. A process for separating components having weight average molecular weights of approximately 2,000 to 4,000 and having weak encephalitogenic activity and high protective activity from the recovered components of claim 1 which comprises dissolving said components in approximately 0.005M to 0.02M ammonium chloride in approximately 0.005M to 0.02M ammonium hydroxide solution, chromatographing on carboxymethylcellulose in the ammonium form, eluting said chromatographed solution with approximately 0.005M to 0.02M ammonium chloride in approximately 0.005M to 0.2M ammonium hydroxide, collecting said first eluate, eluting said chromatographed solution with approximately 0.1M to 0.5M ammonium chloride in approximately 0.1M to 0.5M ammonium hydroxide, collecting said second eluate and recovering three chromatographically distinct products from said eluates, all three having weight average molecular weights of 2,000 to 4,000 weak encephalitogenic activity and a high protective activity.

3. The components obtained from the process of claim 1.

4. The components obtained from the process of claim 2.

5. A process for treating mammals to reduce symptoms of experimentally induced demyelinating diseases, which comprises injecting said mammals after onset of the disease with large successive doses of the components of claim 4.

6. A process for separating components with weight average molecular weights of approximately 8,000 to 10,000 having a high encephalitogenic activity from the crude basic protein derived from defatted mylinated mammalian central nervous system material, which comprises dissolving said mammalian central nervous system material in about 0.05M to about 0.015M sodium carbonate in about 0.01M to about 0.09M ammonium hydroxide solution, chromatographing said solution containing mammalian central nervous system material on carboxymethylcellulose having sodium cations; eluting said chromatographed solution with approximately 0.01M to 0.03M of sodium chloride in approximately 0.01M to 0.09M ammonium hydroxide solution; collecting said first eluate; eluting said chromatographed solution with approximately 0.1M to 0.5M sodium chloride in 0.01M to 0.09M ammonium hydroxide; collecting said second eluate; and recovering said components from said second eluate.

7. A process for separating components with weight average molecular weights of approximately 2,000 to 4,000 having weak encephalitogenic activity and high protective activity from the recovered components of claim 6 which comprises treating said components with about 5N to 7N hydrochloride acid, recovering the crude material, dissolving said crude material in about 0.005M to about 0.015M sodium carbonate in about 0.01M to about 0.09M ammonium hydroxide solution, chromatographing said solution containing said crude material on carboxymethylcellulose having sodium cations and eluting said chromatographed solution with approximately 0.01M to 0.03M of sodium chloride in approximately 0.01M to 0.09M ammonium hydroxide solution, collecting said eluate and recovering said components therefrom.

8. A process for separating components having weight average molecular weights of approximately 2,000 to 4,000 and weak encephalitogenic activity and a high protective activity from the recovered components of claim 7 which comprises, dissolving said components in approximately 0.005M to 0.02M ammonium chloride in approximately 0.005M to 0.02M ammonium hydroxide solution, chromatographing on carboxymethylcellulose in the ammonium form, eluting said chromatographed solution with approximately 0.005M to 0.02M ammonium chloride in approximately 0.005M to 0.2M ammonium hydroxide, collecting said first eluate, eluting said chromatographed solution with approximately 0.1M to 0.5M ammonium chloride in approximately 0.1M to 0.5M ammonium hydroxide, collecting said second eluate and recovering four chromatographically distinct products from said eluates, all four having weight average molecular weights of 2,000 to 4,000, weak encephalitogenic activity and a high protective activity.

9. The components obtained from the process of claim 7.

10. The components obtained from the process of claim 8.

11. A process for treating mammals to reduce symptoms of experimentaly induced demyelinating diseases which comprises injecting said mammals after onset of the disease with large successive doses of the components of claim 10.

* * * * *